United States Patent
Fostick et al.

(10) Patent No.: US 9,724,515 B2
(45) Date of Patent: Aug. 8, 2017

(54) ELECTRICAL SUBSTANCE CLEARANCE FROM THE BRAIN FOR TREATMENT OF ALZHEIMER'S DISEASE

(71) Applicant: RAINBOW MEDICAL LTD., Herzliya (IL)

(72) Inventors: Gideon Fostick, Givat Shmuel (IL); Yossi Gross, Moshav Mazor (IL)

(73) Assignee: RAINBOW MEDICAL LTD., Herzliya (IL)

(*) Notice: Subject to any disclaimer, the term of this patent is extended or adjusted under 35 U.S.C. 154(b) by 0 days.

(21) Appl. No.: 14/926,705

(22) Filed: Oct. 29, 2015

(65) Prior Publication Data
US 2017/0120053 A1    May 4, 2017

(51) Int. Cl.
 *A61N 1/00* (2006.01)
 *A61N 1/36* (2006.01)
 *A61N 1/05* (2006.01)

(52) U.S. Cl.
 CPC ....... *A61N 1/36082* (2013.01); *A61N 1/0534* (2013.01)

(58) Field of Classification Search
 CPC ............ A61N 1/0529–1/0539; A61N 1/36082
 See application file for complete search history.

(56) References Cited

U.S. PATENT DOCUMENTS

| | | | |
|---|---|---|---|
| 4,503,863 A | 3/1985 | Katims | |
| 5,088,977 A | 2/1992 | Sibalis | |
| 5,529,574 A | 6/1996 | Frackelton | |
| 5,792,100 A | 8/1998 | Shantha | |
| 5,911,223 A | 6/1999 | Weaver et al. | |
| 6,041,252 A | 3/2000 | Walker et al. | |
| 6,161,047 A | 12/2000 | King et al. | |
| 6,567,702 B1 | 5/2003 | Nekhendzy et al. | |
| 6,591,138 B1 | 7/2003 | Fischell et al. | |
| 6,602,248 B1 | 8/2003 | Sharps et al. | |
| 6,941,172 B2 | 9/2005 | Nachum | |
| 6,997,941 B2 | 2/2006 | Sharkey et al. | |
| 7,120,489 B2 | 10/2006 | Shalev et al. | |
| 7,398,121 B2 | 7/2008 | Matsumura et al. | |
| 7,509,171 B2 | 3/2009 | DiMauro | |

(Continued)

FOREIGN PATENT DOCUMENTS

| WO | 01/52931 | 7/2001 |
|---|---|---|
| WO | 01/85027 A2 | 11/2001 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Scott Getzow
(74) *Attorney, Agent, or Firm* — Sughrue Mion, PLLC

(57) ABSTRACT

Apparatus is provided that includes a parenchymal electrode, configured to be implanted in brain parenchyma of a subject identified as at risk of or suffering from Alzheimer's disease; and a ventricular electrode, configured to be implanted in a ventricular system of a brain of the subject. Control circuitry is configured to drive the parenchymal and the ventricular electrodes to clear a substance from the brain parenchyma into the ventricular system. Other embodiments are also described.

16 Claims, 4 Drawing Sheets

(56) References Cited

U.S. PATENT DOCUMENTS

| | | |
|---|---|---|
| 7,640,062 B2 | 12/2009 | Shalev |
| 7,860,569 B2 | 12/2010 | Solberg et al. |
| 8,190,248 B2 | 5/2012 | Besio et al. |
| 8,457,761 B2 | 6/2013 | Wariar |
| 8,577,469 B2 | 11/2013 | Gross |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0159790 A1 | 7/2005 | Shalev |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0213700 A1 | 9/2007 | Davison et al. |
| 2008/0119907 A1 | 5/2008 | Stahmann |
| 2008/0260542 A1 | 10/2008 | Nishikawa et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1* | 2/2011 | Alterman ............... A61N 1/044 604/21 |
| 2011/0160638 A1 | 6/2011 | Mauge et al. |
| 2011/0160797 A1 | 6/2011 | Makous et al. |
| 2013/0066392 A1 | 3/2013 | Simon et al. |
| 2013/0166006 A1 | 6/2013 | Williams |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0119898 A1 | 4/2015 | Desalles et al. |
| 2017/0007823 A1 | 1/2017 | Gross |

FOREIGN PATENT DOCUMENTS

| | | |
|---|---|---|
| WO | 2001/085094 | 11/2001 |
| WO | 2006/090397 | 8/2006 |
| WO | 2008/007369 | 1/2008 |
| WO | 2017/006327 A1 | 1/2017 |

OTHER PUBLICATIONS

De La Torre JC, "Vascular Basis of Alzheimer's Pathogensis," Ann NY Acad Sci. 977:196-215 (Nov. 2002).

Weller Ro et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An International Search Report and a Written Opinion both dated Aug. 7, 2008, which issued during the prosecution of Applicant's PCT/IL2007/00865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

An Office Action dated Apr. 11, 2013, which issued during the prosecution of U.S. Appl. No. 13/663,757.

Notice of Allowance dated Oct. 28, 2013, which issued during the prosecution of U.S. Appl. No. 13/663,757.

Elixmann IM et al., "In-vitro evaluation of a drainage catheter with integrated bioimpedance electrodes to determine ventricular size," Biomed Tech 2013; 58 (Suppl. 1) Sep. 2013 (2 pages total).

An Office Action dated Aug. 31, 2015, which issued during the prosecution of U.S. Appl. No. 13/872,794.

An Applicant Initiated Interview Summary dated Dec. 14, 2015, which issued during the prosecution of U.S. Appl. No. 13/872,794.

An Office Action dated Feb. 3, 2016, which issued during the prosecution of U.S. Appl. No. 13/872,794.

An Applicant Initiated Interview Summary dated Feb. 25, 2016, which issued during the prosecution of U.S. Appl. No. 13/872,794.

An Office Action dated Jun. 15, 2016, which issued during the prosecution of U.S. Appl. No. 13/872,794.

An International Search Report and Written Opinion in PCT/IL2016/050728, dated Oct. 20, 2016.

A Notice of Allowance in U.S. Appl. No. 14/794,739, dated Dec. 9, 2016.

International Search Report and Written Opinion in PCT/IL2016/051161, dated Jan. 26, 2017.

A Non-Final Office Action issued in U.S. Appl. No. 15/453,290, dated May 26, 2017.

* cited by examiner

ELECTRICAL SUBSTANCE CLEARANCE FROM THE BRAIN FOR TREATMENT OF ALZHEIMER'S DISEASE

FIELD OF THE APPLICATION

The present invention relates generally to treatment and prevention of Alzheimer's disease, and specifically to electrical techniques for treating, preventing, or slowing the progression of Alzheimer's disease.

BACKGROUND OF THE APPLICATION

Alzheimer's disease is a chronic neurodegenerative disease that causes dementia. Accumulation of substances such as amyloid beta and/or tau protein in the brain is widely believed to contribute to the development of Alzheimer's disease.

US Patent Application Publication 2014/0324128 to Gross, which is assigned to the assignee of the present application and is incorporated herein by reference, describes apparatus for driving fluid between first and second anatomical sites of a subject. The apparatus comprises (1) a first electrode, configured to be coupled to the first anatomical site of the subject; (2) a second electrode, configured to be coupled to the second anatomical site of the subject; and (3) a control unit, configured to (i) detect a pressure difference between the first and second anatomical sites, and (ii) in response to the detected pressure difference, drive fluid between the first and second anatomical sites by applying a treatment voltage between the first and second electrodes. Other embodiments are also described.

SUMMARY OF THE APPLICATION

Some embodiments of the present invention provide techniques for treating Alzheimer's disease. In some applications of the present invention, a parenchymal electrode is implanted in parenchyma of the brain, and a ventricular electrode is implanted in a ventricular system of the brain. Control circuitry is activated to drive the parenchymal and the ventricular electrodes to clear a substance, such as amyloid beta and/or tau protein, from the brain parenchyma into the ventricular system.

There is therefore provided, in accordance with an application of the present invention, apparatus including:

a parenchymal electrode, configured to be implanted in brain parenchyma of a subject identified as at risk of or suffering from Alzheimer's disease;

a ventricular electrode, configured to be implanted in a ventricular system of a brain of the subject; and control circuitry, configured to drive the parenchymal and the ventricular electrodes to clear a substance from the brain parenchyma into the ventricular system.

For some applications, the substance includes amyloid beta, and the control circuitry is configured to drive the parenchymal and the ventricular electrodes to clear the amyloid beta from the brain parenchyma into the ventricular system. For some applications, the substance includes metal ions, and the control circuitry is configured to drive the parenchymal and the ventricular electrodes to clear the metal ions from the brain parenchyma into the ventricular system. For some applications, the substance includes tau protein, and the control circuitry is configured to drive the parenchymal and the ventricular electrodes to clear the tau protein from the brain parenchyma into the ventricular system.

For some applications, the parenchymal electrode is configured to be implanted in white matter of the brain.

For some applications, the control circuitry is configured to configure the parenchymal electrode to be an anode, and the ventricular electrode to be a cathode. For some applications, the control circuitry is configured to configure the parenchymal electrode to be a cathode, and the ventricular electrode to be an anode.

For some applications, the control circuitry is configured to additionally apply deep brain stimulation using the parenchymal electrode.

For some applications, the control circuitry is configured to be implanted under skin of the subject.

For some applications, the control circuitry is configured to drive the parenchymal and the ventricular electrodes to clear the substance by applying a non-excitatory current between the parenchymal and the ventricular electrodes.

For some applications, the control circuitry is configured to drive the parenchymal and the ventricular electrodes to clear the substance by applying direct current between the parenchymal and the ventricular electrodes. For some applications, the control circuitry is configured to apply the direct current with an average amplitude of between 1 and 5 mA. For some applications, the control circuitry is configured to apply the direct current with an average amplitude of less than 1.2 V.

For some applications, the control circuitry is configured to apply the direct current as a series of pulses. For some applications, the control circuitry is configured to apply the direct current as the series of pulses having an average pulse duration of between 100 milliseconds and 300 seconds. For some applications, the control circuitry is configured to apply the direct current as the series of pulses with a duty cycle of between 1% and 50%.

For some applications, the control unit is configured to:

drive the parenchymal and the ventricular electrodes to clear the substance by applying a voltage between the parenchymal and the ventricular electrodes during each of the pulses, while applying the voltage, measure a current resulting from application of the voltage during the pulse, and terminate the pulse upon the measured current falling below a threshold value.

For some applications, the threshold value is based on an initial current magnitude measured upon commencement of the pulse.

There is further provided, in accordance with an application of the present invention, a method including:

implanting a parenchymal electrode in brain parenchyma of a subject identified as at risk of or suffering from Alzheimer's disease;

implanting a ventricular electrode in a ventricular system of a brain of the subject; and activating control circuitry to drive the parenchymal and the ventricular electrodes to clear a substance from the brain parenchyma into the ventricular system.

For some applications, the substance includes amyloid beta, and activating the control circuitry includes activating the control circuitry to drive the parenchymal and the ventricular electrodes to clear the amyloid beta from the brain parenchyma into the ventricular system. For some applications, the substance includes metal ions, and activating the control circuitry includes activating the control circuitry to drive the parenchymal and the ventricular electrodes to clear the metal ions from the brain parenchyma into the ventricular system. For some applications, the substance includes tau protein, and activating the control circuitry includes activating the control circuitry to drive the parenchymal and the ventricular electrodes to clear the tau protein from the brain parenchyma into the ventricular system.

For some applications, implanting the parenchymal electrode in the brain parenchyma includes implanting the parenchymal electrode in white matter of the brain.

For some applications, activating the control circuitry includes activating the control circuitry to configure the parenchymal electrode to be an anode, and the ventricular electrode to be a cathode. For some applications, activating the control circuitry includes activating the control circuitry to configure the parenchymal electrode to be a cathode, and the ventricular electrode to be an anode.

For some applications, the method further includes applying deep brain stimulation using the parenchymal electrode.

For some applications, the method further includes implanting the control circuitry under skin of the subject.

For some applications, activating the control circuitry to drive the parenchymal and the ventricular electrodes includes activating the control circuitry to drive the parenchymal and the ventricular electrodes to clear the substance by applying a non-excitatory current between the parenchymal and the ventricular electrodes.

For some applications, activating the control circuitry to drive the parenchymal and the ventricular electrodes includes activating the control circuitry to drive the parenchymal and the ventricular electrodes to clear the substance by applying direct current between the parenchymal and the ventricular electrodes. For some applications, activating the control circuitry to apply the direct current includes activating the control circuitry to apply the direct current with an average amplitude of between 1 and 5 mA. For some applications, activating the control circuitry to apply the direct current includes activating the control circuitry to apply the direct current with an average amplitude of less than 1.2 V.

For some applications, activating the control circuitry to apply the direct current includes activating the control circuitry to apply the direct current as a series of pulses. For some applications, activating the control circuitry to apply the direct current as the series of pulses includes activating the control circuitry to apply the direct current as the series of pulses having an average pulse duration of between 100 milliseconds and 300 seconds. For some applications, activating the control circuitry to apply the direct current as the series of pulses includes activating the control circuitry to apply the direct current as the series of pulses with a duty cycle of between 1% and 50%.

For some applications, activating the control circuitry to drive the parenchymal and the ventricular electrodes includes activating the control unit to:
drive the parenchymal and the ventricular electrodes to clear the substance by applying a voltage between the parenchymal and the ventricular electrodes during each of the pulses,
while applying the voltage, measure a current resulting from application of the voltage during the pulse, and
terminate the pulse upon the measured current falling below a threshold value.

For some applications, the threshold value is based on an initial current magnitude measured upon commencement of the pulse.

For some applications, implanting the parenchymal and the ventricular electrodes includes implanting the parenchymal and the ventricular electrodes such that an area of build-up of the substance is between the parenchymal and the ventricular electrodes. For some applications, implanting the parenchymal and the ventricular electrodes includes identifying the area of build-up of the substance in the brain parenchyma before implanting the parenchymal and the ventricular electrodes. For some applications, identifying the area of build-up includes performing imaging of the brain. For some applications, performing the imaging includes performing functional MRI (fMRI) imaging of the brain.

For some applications, implanting the parenchymal electrode includes implanting the parenchymal electrode such that an area of build-up of the substance is between the parenchymal electrode and an area of the ventricular system nearest the area of build-up. For some applications, implanting the parenchymal electrode includes identifying the area of build-up of the substance in the brain parenchyma before implanting the parenchymal electrode. For some applications, identifying the area of build-up includes performing imaging of the brain. For some applications, performing the imaging includes performing functional MRI (fMRI) imaging of the brain.

The present invention will be more fully understood from the following detailed description of embodiments thereof, taken together with the drawings, in which:

DETAILED DESCRIPTION OF APPLICATIONS

Figure 1A:
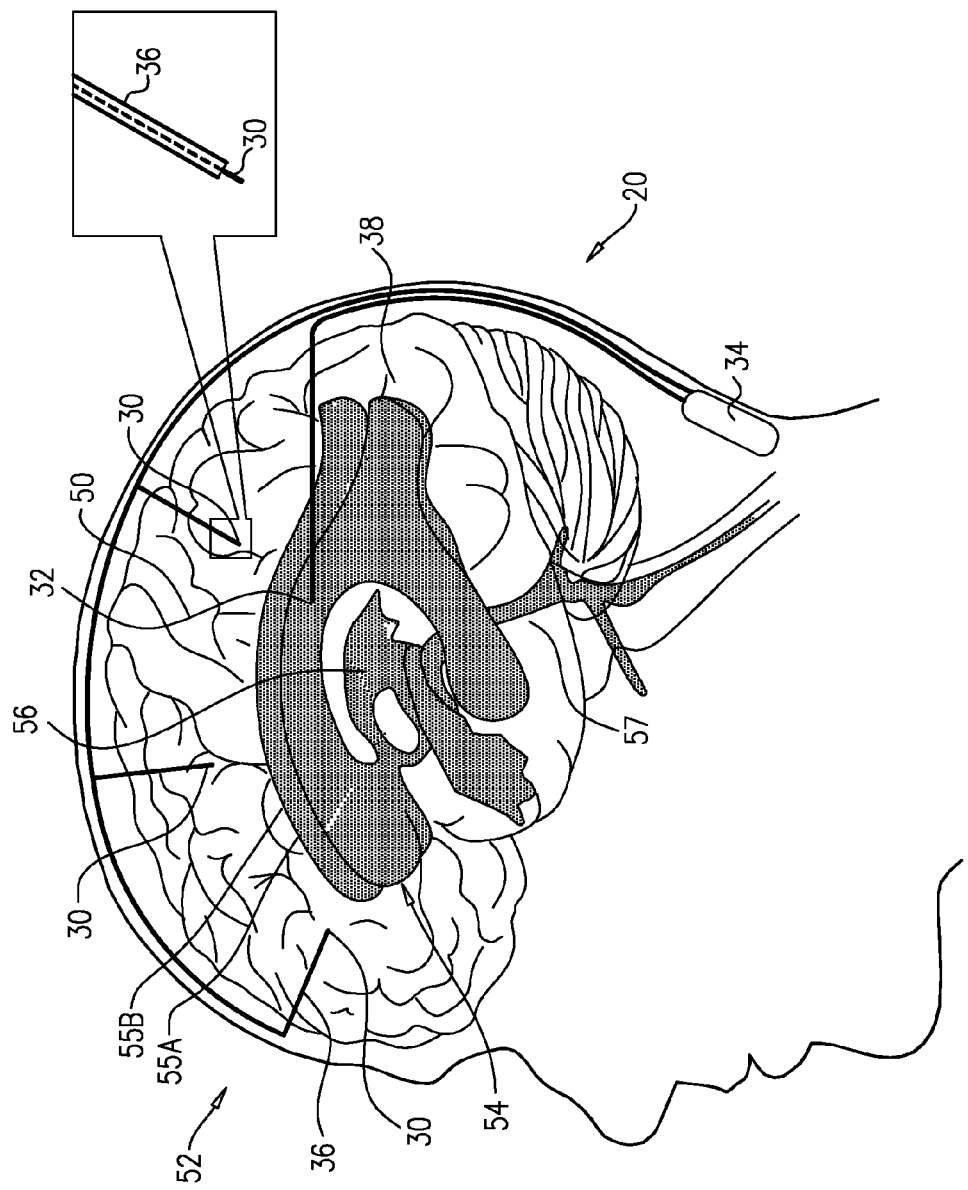
FIGS. 1A, 1B and 1C are schematic illustrations of a system for treating Alzheimer's disease, in accordance with respective applications of the present invention.
Figure 1B:
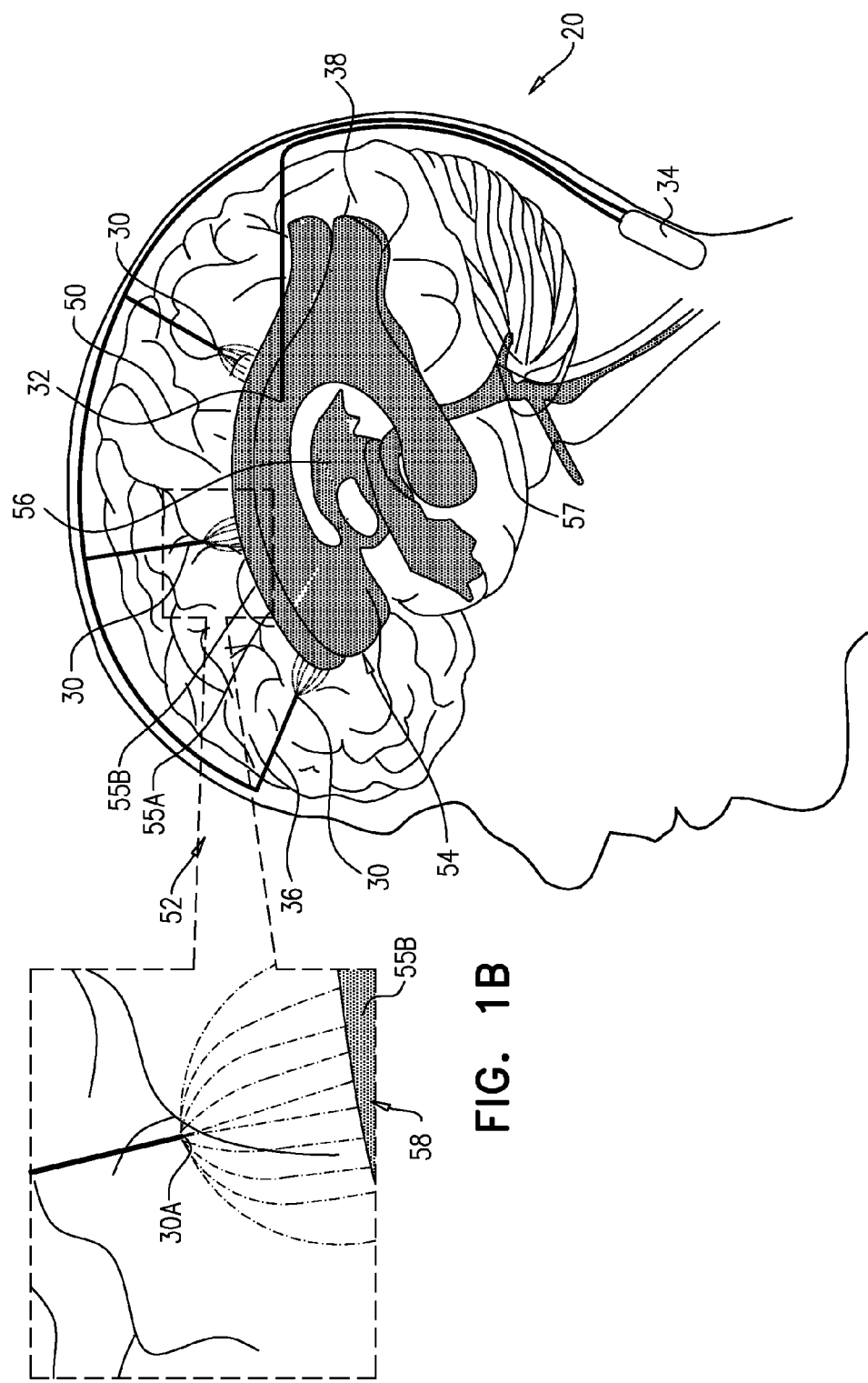
Figure 1C:
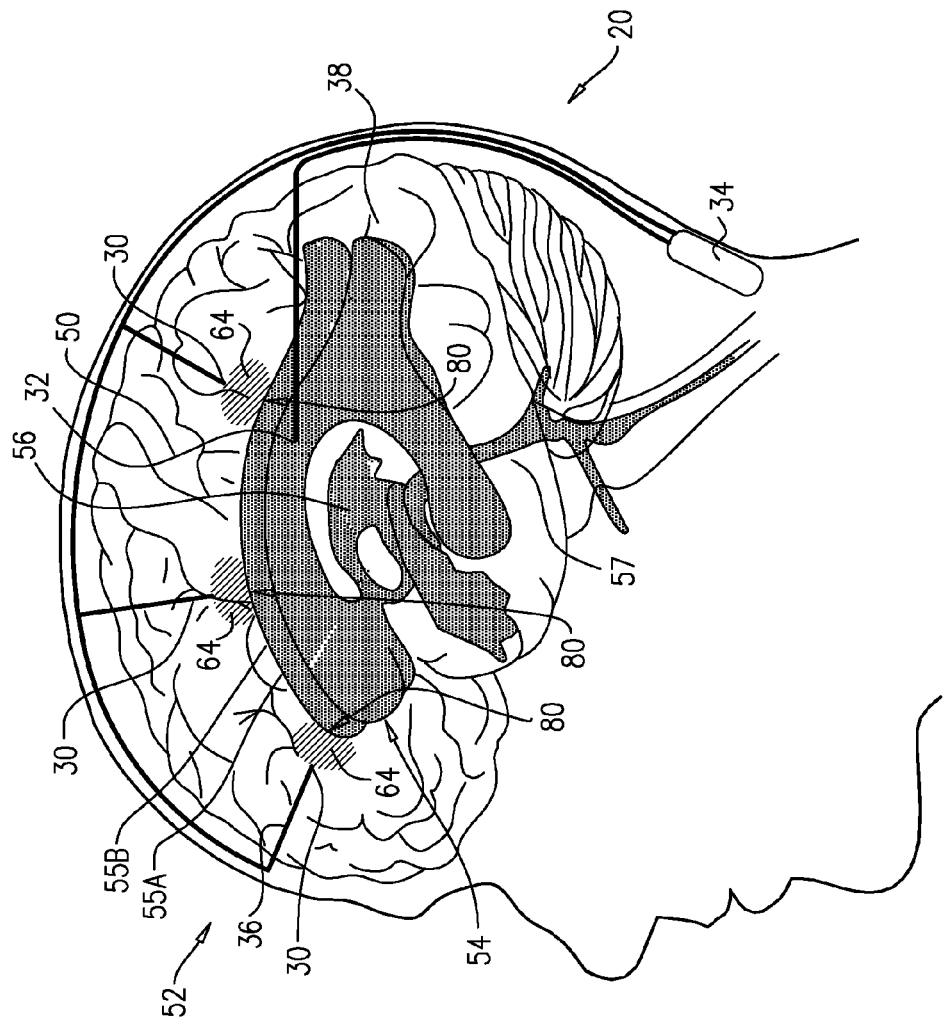

FIGS. 1A, 1B and 1C are schematic illustrations of a system 20 for treating Alzheimer's disease, in accordance with respective applications of the present invention. System 20 comprises parenchymal and ventricular electrodes 30 and 32, and control circuitry 34, which is electrically coupled to parenchymal and ventricular electrodes 30 and 32, typically by parenchymal and ventricular electrode leads 36 and 38, respectively.

In some applications of the present invention, parenchymal electrode 30 is implanted in parenchyma 50 of a brain 52 of a subject identified as at risk of or suffering from Alzheimer's disease, e.g., using techniques similar to those for implantation of electrodes for deep brain stimulation. Ventricular electrode 32 is implanted in a ventricular system 54 of brain 52. For example, ventricular electrode 32 may be implanted using techniques known for implanting hydrocephalus shunts, mutatis mutandis. As used in the present application, including in the claims, ventricular system 54 includes and is limited to lateral ventricles 55 (left and right lateral ventricles 55A and 55B), a third ventricle 56, a fourth ventricle 57, a cerebral aqueduct, interventricular foramina, a median aperture, and left and right lateral apertures.

Control circuitry 34 is activated to drive parenchymal and ventricular electrodes 30 and 32 to clear a substance from brain parenchyma 50 into ventricular system 54. For some applications, the substance comprises amyloid beta, metal ions, a tau protein, and/or a waste substance. As used in the present application, including in the claims, clearing a substance from the brain parenchyma is to be understood as including clearing a portion of the substance, without clearing all of the substance. Typically, in order to clear the substance, control circuitry 34 applies a voltage between parenchymal and ventricular electrodes 30 and 32.

Typically, a healthcare worker, such as a physician, activates control circuitry 34 to provide the functions described herein. Activating the control unit may include configuring parameters and/or functions of the control circuitry (such as using a separate programmer or external controller), or activating the control unit to perform functions pre-programmed in the control circuitry. Control circuitry 34 typically comprises appropriate memory, processor(s), and hardware running software that is configured to provide the functionality of control circuitry described herein.

Current may flow generally through tissue that is located between parenchymal and ventricular electrodes 30 and 32. Alternatively or additionally, at least a portion of the current may flow between (a) parenchymal electrode 30 and (b) an area of the ventricular system 54 nearest parenchymal electrode 30. The inventors have appreciated that because of the low electrical resistance of cerebrospinal fluid (CSF) in ventricular system 54, the ventricles are to some extent a single entity electrically. Therefore, a large portion of the current flows to the nearest portion of ventricular system 54, even if ventricular electrode 32 is implanted in a ventricle remote from parenchymal electrode 30. For example, as shown in FIG. 1B, if a parenchymal electrode 30A is implanted in a right hemisphere of brain 52, most of the current may flow between parenchymal electrode 30A and an area 58 of right ventricle 55B nearest parenchymal electrode 30A, even though ventricular electrode 32 is implanted in left ventricle 55A.

For some applications, the voltage applied between the electrodes may clear the substance electrophoretically, because of a positive or negative charged interface between the surface of the particles of the substance and the surrounding brain tissue fluids. For these applications, the voltage applied between the electrodes causes a potential difference between brain parenchyma 50 and ventricular system 54, which causes movement of the substance from brain parenchyma 50 to ventricular system 54. Alternatively or additionally, for some applications, the voltage applied between the electrodes may clear the substance electroosmotically, because of a positive or negative charge of fluid in the parenchyma. For these applications, the voltage applied between the electrodes causes a potential difference between brain parenchyma 50 and ventricular system 54, which causes increased flow from brain parenchyma 50 to ventricular system 54, and thus increased transport of the substance from parenchyma 50 to ventricular system 54.

For some applications, system 20 comprises a plurality of parenchymal electrodes 30 and/or a plurality of ventricular electrodes 32. Parenchymal electrodes 30 may be implanted in one or both hemispheres of brain 52, and/or at one or more than one location in each of the hemispheres. For some applications, such as shown in FIGS. 1A-C, system 20 comprises a plurality of parenchymal electrodes 30 and exactly one ventricular electrode 32. For example, the single ventricular electrode 32 may be implanted in one of lateral ventricles 55 or third ventricle 56, which, as discussed above, are to a large degree in good electrical connectivity with the other ventricles. For other applications (configuration not shown), system 20 comprises (a) exactly two ventricular electrodes 32, which are implanted in left and right lateral ventricles 55A and 55B, respectively, or (b) exactly three ventricular electrodes 32, which are implanted in left and right lateral ventricles 55A and 55B and third ventricle 56, respectively.

For applications in which system 20 comprises a plurality of parenchymal electrodes 30 and/or a plurality of ventricular electrodes 32, system 20 typically comprises a corresponding plurality of parenchymal electrode leads 36 and/or a corresponding plurality of ventricular electrode leads 38. Each of the leads may comprise separate electrical insulation, and/or a portion of the leads may be joined and share common electrical insulation, as shown in FIGS. 1A-C for parenchymal electrode leads 36. Control circuitry 34 may be activated to independently drive parenchymal electrodes 30, e.g., using separately circuitry. Alternatively, one or more of parenchymal electrodes 30 may be shorted to one another, such that the control circuitry drives the shorted electrodes together. Control circuitry 34 may be activated to drive parenchymal electrodes 30 simultaneously or at different times.

For some applications, brain parenchyma 50 in which parenchymal electrode 30 is implanted comprises white matter of the brain.

As used in the present application, including the claims, "treating" includes both treating a subject already diagnosed with Alzheimer's disease (such as by delaying, slowing, or reversing progression of the disease, e.g., in a patient diagnosed at an early stage), as well as preventing the development of Alzheimer's disease in a subject not diagnosed with the disease and/or asymptomatic for the disease. For example, the techniques described herein may be used to prevent or delay the development of Alzheimer's disease in responsive to detection of an abnormal level of amyloid beta, such as using a blood test or a spinal tap.

For some applications, control circuitry 34 is configured to be implanted subcutaneously, such under skin of the skull of the subject if the housing containing the control circuitry is small, or elsewhere in the subject's body, such as in the upper chest, if the housing of the control circuitry is larger (e.g., includes batteries), with leads through the neck, or optionally in the head. For these applications, control circuitry 34 is typically driven by an external controller that is in wireless or wired communication with control circuitry 34. For some applications, the external controller is mounted on a bed of the subject (e.g., disposed within a mattress), and is configured to activate control circuitry 34 only at night, and/or only when the subject is sleeping. Such nighttime activation may to some degree mimic the natural timing of clearance of the substance (e.g., amyloid beta or tau protein) during sleep. For other applications, control circuitry 34 is configured to be disposed externally to the subject.

For some applications, control circuitry 34 is activated to drive parenchymal and ventricular electrodes 30 and 32 to clear the substance by applying a non-excitatory current between parenchymal and ventricular electrodes 30 and 32, i.e., the current does not cause propagation of action potentials. Thus, in these applications, control circuitry 34 is activated to set parameters of the current such that the current does not affect, or only minimally affects, neuronal activity. Alternatively, the applied current does excite brain tissue, such as to a small extent.

For some applications, control circuitry 34 is activated to drive parenchymal and ventricular electrodes 30 and 32 to clear the substance by applying direct current (DC) between parenchymal and ventricular electrodes 30 and 32. As used in the present application, including in the claims, direct current means a current having a constant polarity; the amplitude of the direct current may or may not vary over time, and may sometimes be zero.

For some applications, control circuitry 34 is activated to apply the direct current with an average amplitude of at least 1 mA, no more than 5 mA, and/or between 1 and 5 mA. Alternatively or additionally, for some applications, control circuitry 34 is activated to apply the direct current with an average amplitude of less than 1.2 V (such an amplitude may avoid electrolysis in the vicinity of one or both of the electrodes).

For some applications, control circuitry 34 is activated to configure parenchymal electrode 30 to be an anode, and ventricular electrode 32 to be a cathode. Alternatively, control circuitry 34 is activated to configure parenchymal electrode 30 to be a cathode, and ventricular electrode 32 to be an anode. For applications in which the voltage applied between the electrodes clears the substance electrophoretically, the selected polarity of the electrodes typically depends on whether the substance has a positive or negative effective charge. Similarly, for applications in which the voltage applied between the electrodes clears the substance electroosmotically, the selected polarity of the electrodes typically depends on whether the fluid has a positive or negative effective charge.

For some applications, control circuitry 34 is activated to apply the direct current as a series of pulses. For some applications, the series of pulses has an average pulse duration of at least 10 milliseconds, no more than 300 seconds, and/or between 10 milliseconds and 300 seconds, such as: (a) at least 10 milliseconds, no more than 100 milliseconds, and/or between 10 and 100 milliseconds, (b) at least 100 milliseconds, no more than 300 seconds (e.g., no more than 500 milliseconds), and/or between 100 and 300 seconds (e.g., between 100 and 500 milliseconds), (c) at least 500 milliseconds, no more than 5 seconds, and/or between 500 milliseconds and 5 seconds, (d) at least 5 seconds, no more than 10 seconds, and/or between 5 and 10 seconds, or (e) at least 10 seconds, no more than 100 seconds, and/or between 10 and 100 seconds. For some applications, the pulses are applied at a frequency of at least 0.001 Hz, no more than 1 kHz, and/or between 0.001 and 1 kHz, such as: (a) at least 100 Hz, no more than 1 kHz, and/or between 100 Hz and 1 kHz, (b) at least 20 Hz, no more than 100 Hz, and/or between 20 and 100 Hz, or (c) at least 1 Hz, no more than 10 Hz, and/or between 1 and 10 Hz. Alternatively or additionally, for some applications, the series of pulses has a duty cycle of at least 1%, no more than 50%, and/or between 1% and 50%, such as: (a) at least 1%, no more than 5%, and/or between 1% and 5%, (b) at least 5%, no more than 10%, and/or between 5% and 10%, (c) at least 10%, no more than 25%, and/or between 10% and 25%, or (d) at least 25%, no more than 50%, and/or between 25% and 50%. Typically, but not necessarily, the duty cycle is no more than 90%, because a given level of applied voltage produces higher current in the tissue if the capacitance in the tissue is allowed to discharge between pulses.

For some of these applications in which control circuitry 34 applies a voltage between parenchymal and ventricular electrodes 30 and 32 in a series of DC pulses, the resulting current decays because of the effects of tissue electrolytes. The current may decay by about two-thirds of its initial magnitude within tens of milliseconds after commencement of application of each pulse. In order to overcome this capacitance effect, control circuitry 34 is activated to apply the voltage intermittently, in order to provide time periods between pulses during which the capacitance discharges.

For some applications, control circuitry 34 is activated to apply the voltage intermittently with a preprogrammed frequency and/or duty cycle. These parameters may be (a) applicable to all patients or a subgroup of patients, (b) set during a calibration procedure upon implantation of the electrodes, or (c) set based on a geometry of placement of parenchymal and/or ventricular electrodes 30 and/or 32. Alternatively, control circuitry 34 is configured to set these parameters in real time by sensing the current resulting from the applied voltage.

For some applications, control circuitry 34 is activated to measure the current resulting from the applied voltage during each of the applied pulses, and to terminate each of the applied pulses when the magnitude of the measured current falls below a threshold value. For example, the threshold value may be a preprogrammed constant, or may be based on (e.g., a percentage of) the initial current magnitude measured upon commencement of the respective pulse. Control circuitry 34 waits during a discharge period before applying the next pulse.

For some applications, control circuitry 34 is activated to apply, between parenchymal and ventricular electrodes 30 and 32, alternating current (AC) in:
  a primary subset of the pulses at a primary polarity selected to electrophoretically and/or electroosmotically clear the substance, at a primary voltage and with a primary average pulse duration, and
  a secondary subset of the pulses at a secondary polarity opposite the primary polarity, at a secondary voltage less than the primary voltage, and with a secondary average pulse duration greater than the primary average pulse duration.

Because of the lower secondary voltage, the secondary subset of the pulses to a large extent does not reverse the clearance of the substance achieved during application of the primary subset of the pulses. This technique may also help avoid electrolysis in the vicinity of one or both of the electrodes, even if the primary voltage is higher than a threshold DC voltage (e.g., 1.2 V) that might otherwise cause electrolysis.

For some applications, such as illustrated in FIG. 1C, parenchymal and ventricular electrodes 30 and 32 are implanted such that one or more areas of build-up 64 of the substance in brain parenchyma 50 is between the electrodes, rather than implanting parenchymal electrode 30 within the area of build-up. For example, the area(s) of build-up may include amyloid plaque and/or tau protein-related nerve tissue tangles. To this end, typically the area of build-up is first identified, for example by performing imaging of brain 52, such as MRI (e.g., functional MRI (fMRI)) or PET imaging of brain 52. As mentioned above, a plurality of parenchymal electrodes 30 and/or a plurality of ventricular electrodes 32 may be implanted, such as if there is more than one area of build-up 64 of the substance.

For some applications, also such as illustrated in FIG. 1C, the one or more parenchymal electrode are implanted such that the one or more areas of build-up 64 are between parenchymal electrode 30A and respective areas 80 of ventricular system 54 nearest areas of build-up 64. Ventricular electrode 32 may or may not be implanted near areas 80. For applications in which ventricular electrode 32 is not implanted near areas 80, the substance of area of build-up 64 may still be driven into nearest areas 80 of ventricular system 54, because nearest areas 80 are in fluid communication with ventricular electrode 32 via CSF of ventricular system 54, as discussed above. As mentioned above, a plurality of parenchymal electrodes 30 and/or a plurality of ventricular electrodes 32 may be implanted, such as if there is more than one area of build-up 64 of the substance, or in general in order to provide good clearance of the substance.

For some applications, parenchymal electrode 30 is further used for applying deep brain stimulation, as is known in the art. For example, the deep brain stimulation may be applied when the electrodes are not being driven to drive the substance into the ventricular system. As is known in the art, the deep brain stimulation may be applied to reduce tremor and block involuntary movements in patients with motion disorders, such as Parkinson's disease, or to treat epilepsy, cluster headaches, Tourette syndrome, chronic pain, or major depression. The implantation location of parenchymal electrode 30 may be selected to be appropriate for the treatment of a particular condition, as well as for clearing the substance.

For some applications, control circuitry 34 is activated to drive parenchymal and ventricular electrodes 30 and 32 in sessions, each of which has a duration of several seconds or several minutes, or continuously for longer periods (e.g., 30 minutes). For some applications, the electrodes are not driven for a period that is at least an hour. Optionally, control circuitry 34 is activated to drive the electrodes only when the subject is sleeping, such as to inhibit any sensations that may be associated with the driving. For some applications, power for activating and/or charging control circuitry 34 is transmitted from a wireless energy transmitter in a device applied to the head, such as a hat, or from a wireless energy transmitter in, under, or above a mattress, such as described hereinabove. For some applications, control circuitry 34 is activated to drive the electrodes according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the control circuitry does not drive the electrodes are provided in the pre-selected schedule.

For any of the applications described herein, ventricular electrode 32 may be implanted in one of the following sites, rather than in ventricular system 54:
- a central canal of the spinal cord (which is in fluid communication with ventricular system 54);
- a superior sagittal sinus (which is in fluid communication with ventricular system 54 because CSF drains into the superior sagittal sinus from ventricular system 54); or
- a subarachnoid space (which is in fluid communication with ventricular system 54 because CSF drains into cisterns of the subarachnoid space via foramina of ventricular system 54).

For any of the applications described herein, parenchymal electrode 30 may be implanted in a superior sagittal sinus, rather than in brain parenchyma 50 (typically, in these applications, ventricular electrode 32 is implanted in ventricular system 54).

For some applications, parenchymal and ventricular electrodes 30 and 32 are implanted in brain parenchyma 50 and ventricular system 54, respectively, and third and fourth electrodes are implanted in the superior sagittal sinus and ventricular system 54, respectively. Control circuitry 34 is activated to apply a first voltage between parenchymal and ventricular electrodes 30 and 32, and a second voltage between the third and the fourth electrodes.

Alternatively, for some applications, parenchymal and ventricular electrodes 30 and 32 are implanted in brain parenchyma 50 and ventricular system 54, respectively, and a third electrode is implanted in the superior sagittal sinus. Control circuitry 34 is activated to apply a first voltage between parenchymal and ventricular electrodes 30 and 32, and a second voltage between ventricular electrode 32 and the third electrode. For some of these applications, control circuitry 34 is activated to set:
- a first polarity of ventricular electrode 32 when applying the first voltage between parenchymal and ventricular electrodes 30 and 32, so as to drive the substance from brain parenchyma 50 into ventricular system 54, and
- a second polarity of ventricular electrode 32, opposite the first polarity, when applying the second voltage between ventricular electrode 32 and the third electrode, so as to drive the substance from ventricular system 54 into the superior sagittal sinus.

Figure 2A:
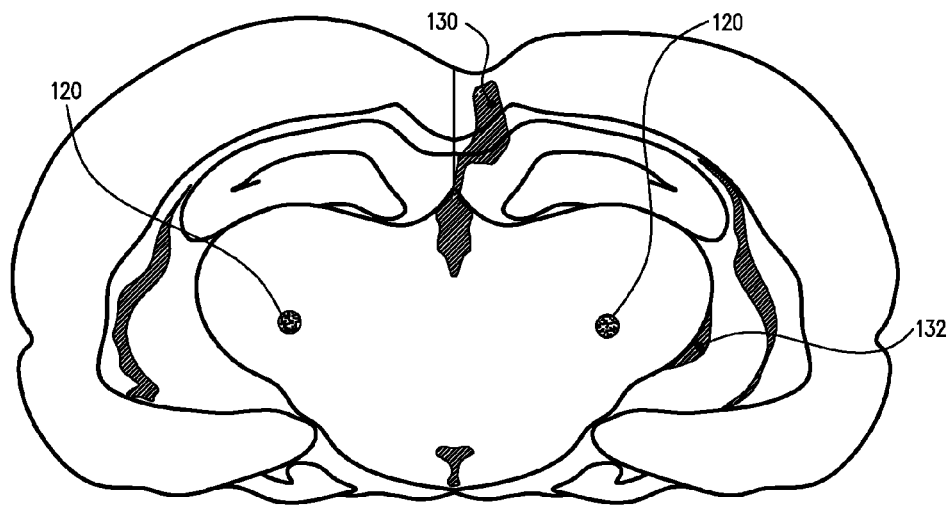
FIGS. 2A-B are schematic illustrations of cross-sections of a rat brain showing results of an animal experiment performed in accordance with an application of the present invention.
Figure 2B:
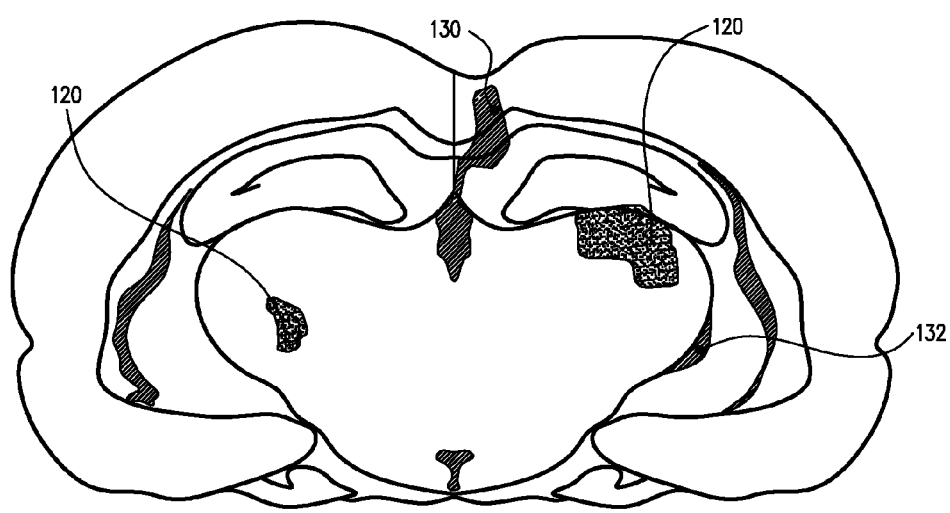

Reference is now made to FIGS. 2A-B, which are schematic illustrations of cross-sections of a rat brain showing results of an animal experiment performed in accordance with an application of the present invention. A rat was anesthetized, a first electrode 130 (a piece of Pt—Ir wire soldered to a miniature connector) was inserted through a hole into the sagittal sinus, and a second electrode 132 (a pieces of Pt—Ir wire soldered to a small electronic connector) was inserted through a hole in dura mater into the right lateral ventricle.

As shown in FIG. 2A, bromephenol blue dye was stereotaxically delivered into both hemispheres of the rat brain at designated coordinates 120 and 122. By using the left hemisphere as a diffusion control, this experimental setup allowed pairwise comparisons within the same animal, thereby ruling out any other effects that might effect a directed migration of the dye in the brain.

Control circuitry was activated to apply a constant-polarity (DC) current to only the right hemisphere, between first and second electrodes 130 and 132, configuring first electrode 130 as a cathode and second electrode 132 as an anode, because bromephenol blue dye comprises effectively anionic (negatively-charged) molecules. The current was applied by repeatedly alternating between two modes: (a) a first mode, in which the current was applied continuously for 5 minutes at a magnitude of 1-2 mA, and (b) a second mode, in which the current was applied in 10-ms-duration pulses, one pulse per second (i.e., a pulse frequency of 1 Hz), at a magnitude of 1-2 mA.

FIG. 2B shows the displacement of the bromephenol blue dye after application of the current to the right hemisphere. As can be seen, the bromephenol blue dye in the left hemisphere experienced minimal dispersion and no directed displacement. In contrast, in the right hemisphere, the applied current moved the bromephenol blue dye toward the lateral ventricle. The dye moved with the average velocity of 0.28+/−0.006 mm/min, which was more than 14 times greater than the observed diffusion rate in the left hemisphere. In the right hemisphere, the linear displacement of the dye profile center was about 1.9±0.08 mm, while the front of the dye profile reached a maximum distance of about 2.81±0.07 mm from the center of the injection point.

The results of this experiment demonstrated that molecules of dye can be moved within brain tissue by applying a DC current using two electrodes implanted in the brain, and that in such a setup, a natural migration path is toward the ventricles. The inventors believe that application of the current between the electrodes may have moved the dye electrophoretically. The inventors also believe that implantation of the first electrode directly in brain parenchyma, rather than in the sagittal sinus, may provide even better current-driven movement of molecules, because the resistance of the parenchyma-sinus interface was calculated as more than two-fold higher than the resistance measured within the parenchyma, based on data collected during the experiment.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. application Ser. No. 13/872,794, filed Apr. 20, 2013, which published as US Patent Application Publication 2014/0324128; and U.S. application Ser. No. 14/794,739, filed Jul. 8, 2015, which published as US Patent Application Publication 2017/0007823.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
a parenchymal electrode, configured to be implanted in brain parenchyma of a subject identified as at risk of or suffering from Alzheimer's disease;
a ventricular electrode, configured to be implanted in a ventricular system of a brain of the subject; and
control circuitry, configured to drive the parenchymal and the ventricular electrodes to clear a substance from the brain parenchyma into the ventricular system by applying direct current between the parenchymal and the ventricular electrodes using an average voltage of less than 1.2 V, the substance comprising one or more substances selected from the group of substances consisting of: amyloid beta, tau protein, and metal ions.

2. The apparatus according to claim 1, wherein the substance includes amyloid beta, and wherein the control circuitry is configured to drive the parenchymal and the ventricular electrodes to clear the amyloid beta from the brain parenchyma into the ventricular system.

3. The apparatus according to claim 1, wherein the substance includes tau protein, and wherein the control circuitry is configured to drive the parenchymal and the ventricular electrodes to clear the tau protein from the brain parenchyma into the ventricular system.

4. The apparatus according to claim 1, wherein the control circuitry is configured to drive the parenchymal and the ventricular electrodes to clear the substance by applying the direct current as non-excitatory current between the parenchymal and the ventricular electrodes.

5. The apparatus according to claim 1, wherein the control circuitry is configured to apply the direct current as a series of pulses.

6. The apparatus according to claim 5, wherein the control circuitry is configured to apply the direct current as the series of pulses having an average pulse duration of between 100 milliseconds and 300 seconds.

7. The apparatus according to claim 5, wherein the control unit is configured to:
measure a current resulting from application of voltage during each of the pulses, and
terminate the pulse upon the measured current falling below a threshold value.

8. A method comprising:
implanting a parenchymal electrode in brain parenchyma of a subject identified as at risk of or suffering from Alzheimer's disease;
implanting a ventricular electrode in a ventricular system of a brain of the subject; and
activating control circuitry to drive the parenchymal and the ventricular electrodes to clear a substance from the brain parenchyma into the ventricular system by applying direct current between the parenchymal and the ventricular electrodes using an average voltage of less than 1.2 V, the substance comprising one or more substances selected from the group of substances consisting of: amyloid beta, tau protein, and metal ions.

9. The method according to claim 8, wherein the substance includes amyloid beta, and wherein activating the control circuitry comprises activating the control circuitry to drive the parenchymal and the ventricular electrodes to clear the amyloid beta from the brain parenchyma into the ventricular system.

10. The method according to claim 8, wherein the substance includes tau protein, and wherein activating the control circuitry comprises activating the control circuitry to drive the parenchymal and the ventricular electrodes to clear the tau protein from the brain parenchyma into the ventricular system.

11. The method according to claim 8, wherein activating the control circuitry to drive the parenchymal and the ventricular electrodes comprises activating the control circuitry to drive the parenchymal and the ventricular electrodes to clear the substance by applying the direct current as non-excitatory current between the parenchymal and the ventricular electrodes.

12. The method according to claim 8, wherein activating the control circuitry to apply the direct current comprises activating the control circuitry to apply the direct current as a series of pulses.

13. The method according to claim 12, wherein activating the control circuitry to apply the direct current as the series of pulses comprises activating the control circuitry to apply the direct current as the series of pulses having an average pulse duration of between 100 milliseconds and 300 seconds.

14. The method according to claim 12, wherein activating the control circuitry to drive the parenchymal and the ventricular electrodes comprises activating the control unit to:
measure a current resulting from application of voltage during each of the pulses, and
terminate the pulse upon the measured current falling below a threshold value.

15. The method according to claim 8, wherein implanting the parenchymal and the ventricular electrodes comprises implanting the parenchymal and the ventricular electrodes such that an area of build-up of the substance is between the parenchymal and the ventricular electrodes.

16. The method according to claim 8, wherein implanting the parenchymal electrode comprises implanting the parenchymal electrode such that an area of build-up of the substance is between the parenchymal electrode and an area of the ventricular system nearest the area of build-up.

* * * * *